United States Patent [19]

Vogt

[11] Patent Number: 5,711,667
[45] Date of Patent: Jan. 27, 1998

[54] ORTHODONTIC BITE JUMPING DEVICE

[76] Inventor: William Vogt, R.D. 4, Box 4205, Bangor, Pa. 18013

[21] Appl. No.: 541,474

[22] Filed: Oct. 10, 1995

Related U.S. Application Data

[63] Continuation-in-part of Ser. No. 287,216, Aug. 8, 1994, abandoned.

[51] Int. Cl.$^6$ ............................................. A61C 7/36
[52] U.S. Cl. ..................................... 433/19; 433/21
[58] Field of Search .............................. 433/18, 19, 20, 433/21

[56] References Cited

U.S. PATENT DOCUMENTS

| | | | |
|---|---|---|---|
| 741,687 | 10/1903 | MacDowell | 433/5 |
| 3,121,953 | 2/1964 | Asher | 433/5 |
| 3,137,941 | 6/1964 | Andrews | 433/5 |
| 3,315,359 | 4/1967 | Moss | 433/17 |
| 3,618,214 | 11/1971 | Armstrong | 433/19 |
| 3,798,773 | 3/1974 | Northcutt | 433/19 |
| 3,997,970 | 12/1976 | Hodgson | 433/19 |
| 4,439,149 | 3/1984 | Devincenzo | 433/6 |
| 4,462,800 | 7/1984 | Jones | 433/19 |
| 4,472,138 | 9/1984 | Howe | 433/19 |
| 4,551,095 | 11/1985 | Mason | 433/19 |
| 4,708,646 | 11/1987 | Jasper | 433/19 |
| 4,795,342 | 1/1989 | Jones | 433/19 |
| 5,022,855 | 6/1991 | Jeckel | 433/18 |
| 5,074,784 | 12/1991 | Sterrett et al. | 433/18 |
| 5,120,218 | 6/1992 | Hanson | 433/19 |
| 5,183,388 | 2/1993 | Kumar | 433/19 |
| 5,299,935 | 4/1994 | Lokar | 433/21 |
| 5,352,116 | 10/1994 | West | 433/19 |

FOREIGN PATENT DOCUMENTS

| | | | |
|---|---|---|---|
| 579422 | 1/1994 | European Pat. Off. | 433/21 |

*Primary Examiner*—Stephen R. Funk
*Attorney, Agent, or Firm*—Gregory J. Gore

[57] ABSTRACT

An orthodontic bite jumping device includes a metal cylinder for receiving a telescoping plunger, for attachment to and between the orthodontic braces fixed to a patient's upper and lower teeth to achieve desired movement in otherwise conventional fashion. This appliance is at each end provided with connectors which slidingly interact with the orthodontic braces. A spring is attached between the cylinder and the plunger in a manner which causes the application of relatively consistent pushing forces to the teeth, to achieve desired tooth and jaw movements while buffering the relatively heavy forces that are produced so as not to cause damage to the orthodontic braces or to the appliances which interconnect them. Such forces are applied to and between the orthodontic braces in a substantially horizontal direction, avoiding the application of major forces in a vertical direction as was characteristic of prior bite jumping devices. The bite jumping device is further provided with a stop mechanism for preventing separation of the telescoping elements when the patient's mouth is fully opened, while otherwise ensuring free movement of the patient's jaws.

7 Claims, 4 Drawing Sheets

ORTHODONTIC BITE JUMPING DEVICE

This application is a continuation-in-part of application Ser. No. 08/287,216 filed Aug. 8, 1994 now abandoned.

BACKGROUND OF THE INVENTION

The present invention relates generally to orthodontic devices, and in particular, to so-called "bite jumping" devices for treating dental protrusion of the upper teeth relative to the lower teeth, as well as misalignments of the teeth and jaws.

A variety of orthodontic devices have been used to achieve realignments of the teeth and jaws. Generally speaking, this involves the application of suitable devices to the upper teeth and/or to the lower teeth of the patient, and the connection of suitable appliances to and between the devices associated with the patient's upper and lower teeth for the purpose of applying relatively consistent forces which are capable of achieving desired tooth and jaw movements.

As an example, in treatments performed for the purpose of bringing the lower jaw forward relative to the upper jaw, removable plastic appliances have often been used. However, such appliances were found to be relatively bulky and cumbersome, and had to be removed to eat or brush the teeth. This led to the disadvantage that removable appliances are often lost or broken. What is more, such appliances tended to distort the patient's speech, often severely, and could at times invoke a gag response from the patient. This led to the disadvantage that patients would often not wear the appliances for a sufficient number of hours to achieve an acceptable treatment. Also to consider is that such appliances have to be fitted, and must therefore be custom made for each patient in a dental laboratory. Laboratory construction leads to the disadvantages of significant cost, and increased treatment times resulting from the relatively long periods needed to construct the desired appliance.

As an alternative to this, various types of fixed, bite jumping appliances have been developed. Such appliances are particularly useful in retrusion of the lower jaw, and examples may be found with reference to U.S. Pat. No. 3,798,773 (Northcutt), U.S. Pat. No. 4,462,800 (Jones), U.S. Pat. No. 4,551,095 (Mason), U.S. Pat. No. 4,708,646 (Jasper) and U.S. Pat. No. 5,183,388 (Kumar).

All except U.S. Pat. No. 4,708,646 disclose variations of a device generally known as a "Herbst" device, which employs a metal cylinder containing a plunger and which is attachable to and between suitable orthodontic appliances (braces) fixed to the patient's upper and lower teeth. Although "Herbst" devices have successfully been used to accomplish various treatments, it has been found that in practice, such devices can exhibit certain disadvantages (see, e.g., White, "Current Herbst Appliance Therapy", *Journal of Clinical Orthodontics*, Vol. 28, No. 5, pages 296–307 (1994), at pages 298–99, 302–04 and 307).

For example, while appliances of this type can be used to perform various tooth movements, such devices are best suited to producing the relatively heavy forces needed for orthopedic movements (e.g., moving the lower jaw forward) and are not particularly well suited to the treatment of malocclusions of the teeth that are not related to underlying skeletal defects (i.e., misalignments of the jaw). Yet, such appliances are designed for rigid attachment to a patient's existing orthodontic braces, or to fixed or removable tooth-covering templates (which are generally fabricated in a laboratory). As a consequence of this, while such devices have found wide acceptance for producing the orthopedic movements necessary to perform various treatments, it has also been found that because of the relatively heavy forces that are produced by such devices (e.g., as the patient's jaws are closed), it is not uncommon for such devices to become damaged, or to cause damage to the orthodontic appliances to which they are attached.

As an example, the above-mentioned U.S. Pat. No. 3,798,773 (Northcutt) describes an appliance including telescoping cylinders for containing a compression spring, and attachable to and between a patient's orthodontic braces. The disclosed appliance has fixed attachment points at each end. As a result, the relatively large forces that are developed are caused to be applied directly to the attachment points. This tends to either break or severely damage the patient's orthodontic braces, or the bite jumping appliance which interconnects them.

Recognizing this potential for breakage (at the point of attachment with the orthodontic braces, and the appliances themselves), steps have been taken to improve the manner in which such appliances are attached to and between the orthodontic braces. The above-mentioned U.S. Pat. No. 4,551,095 (Mason) and U.S. Pat. No. 5,183,388 (Kumar) are examples of this. However, even the replaceable attachment screws which are suggested by these patents do not operate to directly improve upon the basic problem, that being breakage due to the relatively heavy forces that are encountered between the orthodontic braces and the appliances that interconnect them. U.S. Pat. No. 4,551,095 additionally suggests some free movement of the appliances relative to the orthodontic braces. However, the disclosed improvement is insufficient to achieve the desired effect, and a significant potential for damage and breakage still remains.

U.S. Pat. No. 4,708,646 replaces the more conventional Herbst device with an elastic element comprised of a spring surrounded by a rubber core and having metal end caps for attachment to and between the orthodontic appliances associated with the patient's upper and lower teeth. In use, the disclosed elastic element tends to produce extremely high forces, similar to the Herbst device, and is highly susceptible to breakage. Breakage primarily results from the ability of such a device to swivel about its attachment points, producing significant flexure and permitting the device to at times become caught between the patient's upper and lower teeth (and chewed upon). Separation of the end caps from the connecting spring and cover is quite common as a result.

Conventional Herbst appliances are also subject to the disadvantage that the telescoping cylinders can separate when the patient's mouth is opened wide, in turn causing the telescoping cylinders to separate from one another. When the patient's mouth is closed, it is not uncommon for exposed end portions of the telescoping cylinders to come into contact with adjacent portions of the patient's mouth, leading to the potential for cheek ulceration. Yet another problem is the detachment of removable connection screws (if employed) over time, and the potential for lip and cheek irritation which can result from the use of such structures.

Consequently, the need remains to provide a device for appropriately directing the forces that are produced in conjunction with conventional bite jumping devices, or other devices for achieving desired orthodontic treatments, which are less subject to the foregoing disadvantages.

SUMMARY OF THE INVENTION

It is therefore the primary object of the present invention to provide an improved orthodontic bite jumping appliance.

It is also an object of the present invention to provide an improved orthodontic bite jumping appliance for the treatment of dental protrusion of a patient's upper teeth relative to the patient's lower teeth.

It is also an object of the present invention to provide an orthodontic bite jumping appliance having structural elements that are less susceptible to breakage, and to damage of the orthodontic braces with which they are used.

It is also an object of the present invention to provide an orthodontic bite jumping appliance that is less susceptible to breakage, and to damage of the orthodontic braces with which they are used, by providing a limited degree of shock absorption when in use.

It is also an object of the present invention to provide an orthodontic bite jumping appliance that incorporates sliding elements which will not separate from one another when in use.

It is also an object of the present invention to provide an orthodontic bite jumping appliance having characteristics that promote its being worn by the patient.

It is also an object of the present invention to provide an orthodontic bite jumping appliance that is comfortable to wear, unobtrusive, and cosmetically acceptable.

It is also an object of the present invention to provide an orthodontic bite jumping appliance that can provide relatively consistent forces throughout a desired orthodontic procedure.

It is also an object of the present invention to provide an orthodontic bite jumping appliance which is simple in construction, and easy to install and adjust.

These and other objects which will become apparent are achieved in accordance with the present invention by providing an orthodontic bite jumping appliance having various improvements which combine to effectively interconnect the braces associated with a patient's upper and lower teeth with a significantly reduced potential for breakage, while preventing separation of the telescoping elements of the appliance when in use. To this end, each appliance includes an outer cylinder for receiving a telescoping plunger, for attachment to and between the orthodontic braces fixed to a patient's upper and lower teeth to achieve desired movements in otherwise conventional fashion. However, in accordance with the present invention, the appliance is at each end provided with connectors which slidingly interact with the orthodontic braces (e.g., with their arch wires) in a manner which causes the application of relatively consistent pushing forces to the teeth, to achieve desired tooth and jaw movements, while buffering the relatively heavy forces that are produced so as not to cause damage to the orthodontic braces or to the appliances which interconnect them.

The sliding interconnection which is developed also leads to the advantage that any active forces will be applied to the teeth only after the patient's mouth has been substantially closed. As a result, such forces are applied to and between the orthodontic braces in a substantially horizontal direction, avoiding relatively large vertical forces which were often characteristic of prior bite jumping devices. This is accomplished while preserving the potential for developing limited (relatively small) forces in a vertical direction, if appropriate to a particular orthodontic treatment (such as for slight intrusion of the upper molars).

The sliding connection which is developed also allows the telescoping elements of the bite jumping appliance to be provided with a stop mechanism for preventing separation of the telescoping elements when the patient's mouth is fully opened, while otherwise ensuring free movement of the patient's jaws (which would have been compromised by the use of stop mechanisms with prior bite jumping appliances).

For further detail regarding the orthodontic bite jumping device of the present invention, reference is made to the description which is provided below, taken in conjunction with the following illustrations.

BRIEF DESCRIPTION OF THE DRAWINGS

In the several views provided, like reference numbers denote similar structure.

DETAILED DESCRIPTION OF PREFERRED EMBODIMENTS

Figure 1:
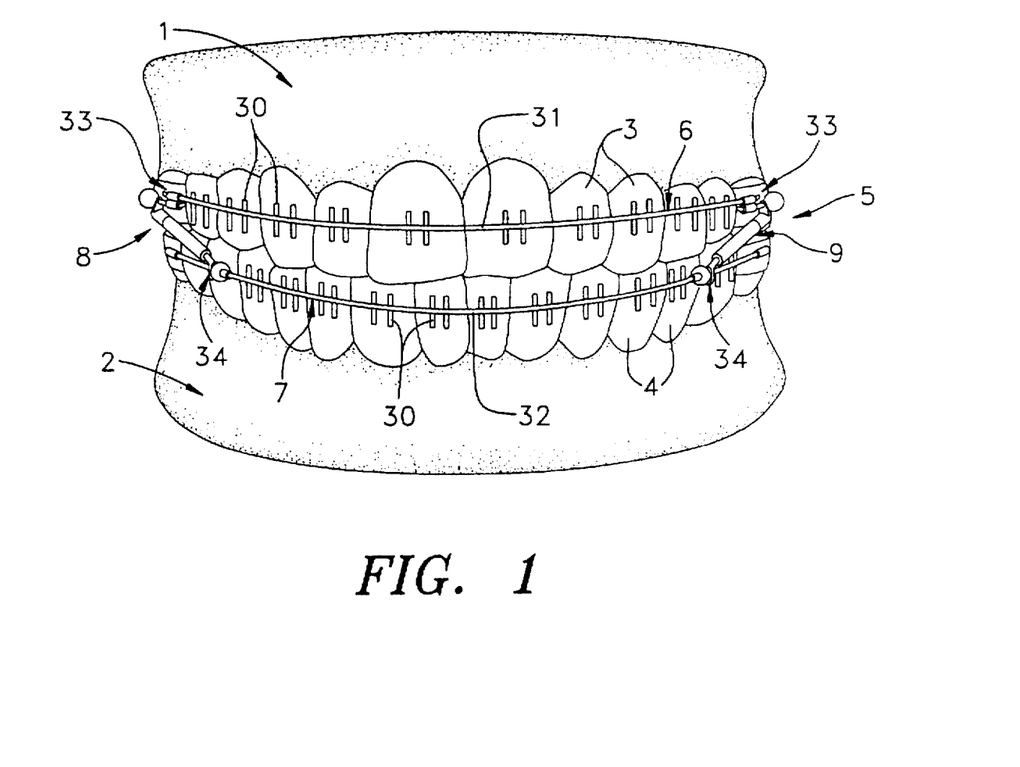
FIG. 1 is an elevational view showing an orthodontic appliance incorporating the connecting devices of the present invention, as viewed from the front of the patient's mouth.
Figure 2:
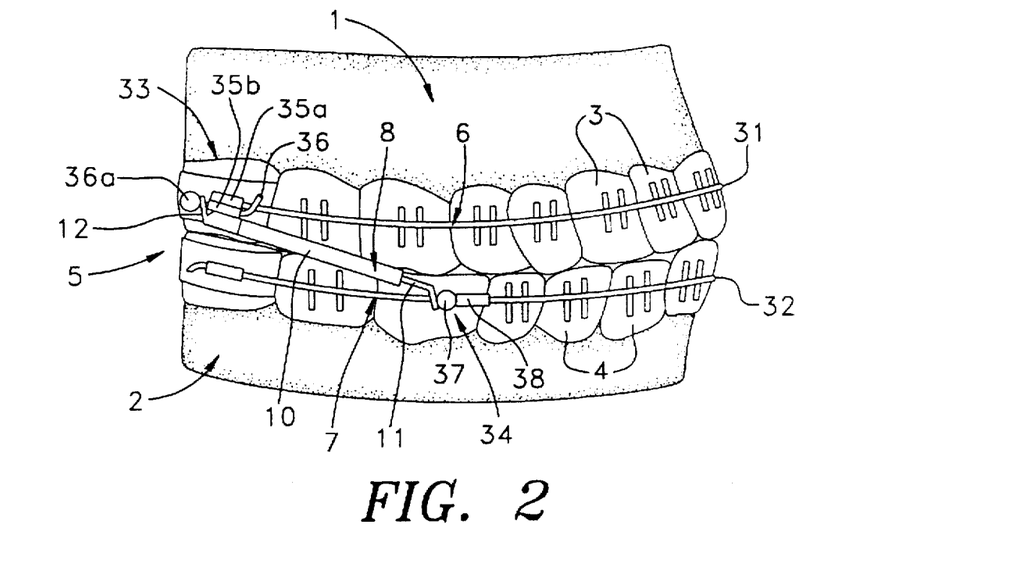
FIG. 2 is an elevational view showing the orthodontic appliance of FIG. 1, as viewed from the side of the patient's mouth.

FIGS. 1 and 2 illustrate the upper jaw 1 and the lower jaw 2 of a hypothetical patient. Upper teeth 3 are associated with the upper jaw 1 and lower teeth 4 are associated with the lower jaw 2. An orthodontic appliance 5 is applied to and between the upper and lower teeth 3, 4 to achieve desired movements of the upper jaw 1 and the lower jaw 2 relative to each other. The discussion which follows is primarily directed to relative movements of this general type. However, it is to be understood that the improvements of the present invention are applicable to any of a number of orthodontic procedures other than those which will be specifically described below. Such orthodontic procedures will be readily understood by the person of ordinary skill in the art, and are achievable by causing the various elements of the orthodontic appliance 5 to interact with the teeth 3, 4, and if desired, the jaws 1, 2, employing techniques that are themselves known and conventional.

The orthodontic appliance 5 is generally comprised of an upper appliance 6 associated with the upper teeth 3, a lower appliance 7 associated with the lower teeth 4, and in the illustrative embodiment shown in FIGS. 1 and 2, a pair of connecting devices 8, 9 interconnecting the upper appliance 6 and the lower appliance 7. The connecting device 8 extends between left-most portions of the upper appliance 6 and left-most portions of the lower appliance 7, while the connecting device 9 extends between right-most portions of the upper appliance 6 and right-most portions of the lower appliance 7. Specifics regarding such attachment will be discussed more fully below.

Figure 3:
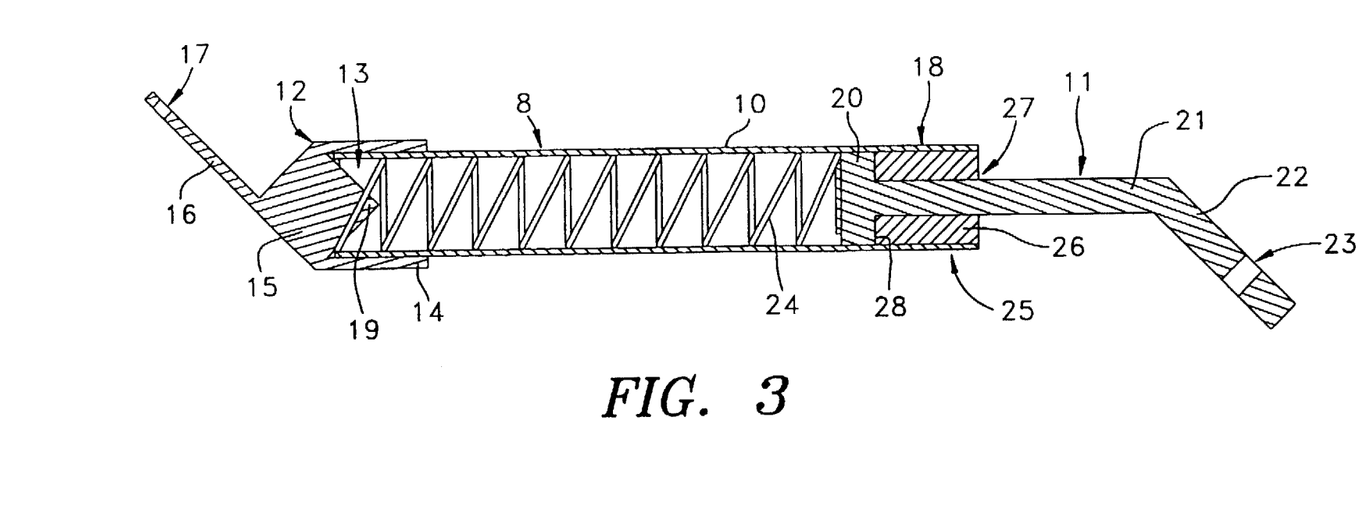
FIG. 3 is a longitudinal cross-sectional view of a preferred embodiment connecting device of the present invention.
Figure 4A:
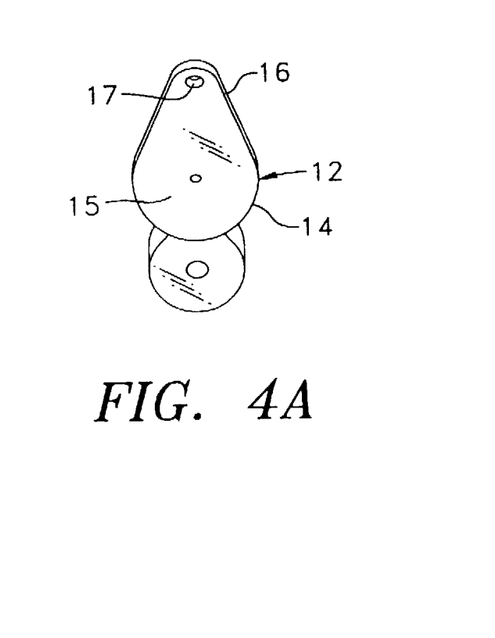
FIG. 4A is an end elevational view of the connecting device, as viewed from the left in FIG. 3.
Figure 4B:
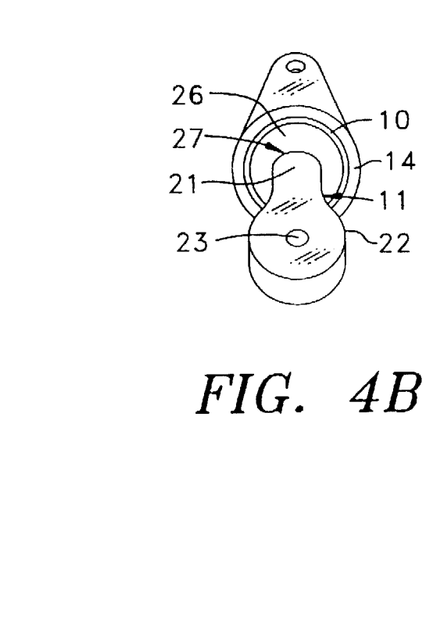
FIG. 4B is an end elevational view of the connecting device, as viewed from the right in FIG. 3.

Construction of the connecting devices 8, 9 is best understood with reference to FIGS. 3, 4A and 4B. Overall construction of the connecting devices 8, 9 is substantially the same. As will be discussed more fully below, interaction between the connecting devices 8, 9 and the upper and lower appliances 6, 7 is readily achievable by correctly positioning the elements of the connecting devices 8, 9 for effective placement along either left-most portions or right-most portions of the orthodontic appliance 5, or both, depending upon the particular treatment which is to take place. Consequently, further discussion of the overall construction of the connecting devices 8, 9 will proceed with reference to the connecting device 8 which is shown in FIGS. 3, 4A and 4B.

Referring now to FIG. 3, the connecting device 8 is generally comprised of an outer cylinder or tube 10, and an inner piston 11, which are in telescoping engagement with one another. The outer tube 10 is preferably hollow at both ends, for ease of manufacture, and receives an end cap 12 for enclosing one of its ends (the end 13). The end cap 12 generally includes a flange 14 for overlying the end 13 of the outer tube 10, a body 15 for enclosing the end 13 of the outer tube 10, and a clip portion 16 having an aperture 17 for engaging portions of the orthodontic appliance 5 as will be discussed more fully below. The piston 11 generally includes a piston body 20 for enclosing the remaining end (the end 18) of the outer tube 10, a piston rod 21 extending from the piston body 20 (and from the end 18 of the outer tube 10) and a clip portion 22 having an aperture 23 for engaging portions of the orthodontic appliance 5 as will be discussed more fully below. A spring 24 is slidingly received in the outer tube 10, and is positioned between the body 15 of the end cap 12 and the piston body 20 of the piston 11 to produce the forces needed for the orthodontic treatment to be performed.

Any of a variety of materials may be used to form the various components of the connecting device 8. Virtually all of the elements of the connecting device 8, including its outer tube 10, the piston 11, the end cap 12 and the spring 24, may be formed of any material which is appropriate to orthodontic treatment, and which is inert in the mouth of the patient. A variety of plastics are useful for this purpose, as are a variety of metals, including but not limited to stainless steel, titanium, nickel-titanium and carbon fiber resins. Preferably, both the outer tube 10 and the piston body 20 are cylindrical in shape, so that the outer tube 10 and the piston 11 can rotate relative to each other. However, in certain circumstances it may be useful for either the outer tube 10, the piston body 20, or both structures to have other shapes which are useful in achieving desired treatments. This could include similar shapes configured for mated engagement (e.g., paired triangular or paired rectangular structures), or dissimilar shapes configured for corresponding engagement (e.g., a squared piston body surrounded by a cylindrical tube). The structural elements of the end cap 12, particularly its flange 14 and body 15, will also tend to vary with the shape selected for the outer tube 10.

Assembly of the connecting device 8 of FIG. 3 generally proceeds as follows. The end cap 12 is positioned over the end 13 of the outer tube 10, and is preferably fixed or bonded to the outer tube 10 to securely retain the two elements together (although a frictional engagement could be employed, if desired). The spring 24 is then placed in the outer tube 10, resting against the body 15 of the end cap 12. To this end, the body 15 preferably includes a projection 19 for receiving and centering the spring 24 within the outer tube 10. The projection 19 may further be formed of an elastomeric material, if desired, to assist in the absorption of shock when the connecting device 8 is in use. In any event, the piston 11 is then inserted into the end 18 of the outer tube 10 so that the piston body 20 faces the spring 24 and slidingly engages the outer tube 10, and so that the piston rod 21 and the clip portion 22 project from the end 18 of the outer tube 10.

While it is possible for assembly of the connecting device 8 to proceed only to this point, leaving the piston 11 free to separate from the outer tube 10, it is preferred in accordance with the present invention to securely retain the piston 11 within the outer tube 10 by providing the end 18 of the outer tube 10 with an appropriate stop mechanism 25 for retaining the piston body 20 (and accordingly, the piston 11) within the outer tube 10. A variety of devices may be used for this purpose.

For example, as illustrated in FIG. 3, the end 18 of the outer tube 10 can be provided with a closure member 26 for enclosing the piston body 20 within the outer tube 10. If desired, the closure member 26 can take the form of a separate element, either fixed or bonded to, or frictionally engaged with the end 18 of the outer tube 10. However, it is considered preferable for the closure member 26 to be formed directly in the end 18 of the outer tube 10, as a chamfered or detented portion configured to effectively engage the piston body 20 and thereby prevent separation of the piston 11 from the outer tube 10. This is preferred since the closure member 26 can then be machined as part of the outer tube 10, representing a convenient means for its manufacture. In such case, overall assembly of the connecting device 8 may have to be varied to accommodate a permanent end closure (e.g., the piston body 20 and the piston rod 21 of the piston 11 may have to be assembled from opposite sides of the closure member 26). In any event, the implementation used will vary depending upon the treatment involved, the environment intended for the connecting device 8, and the materials used in forming the various elements of the connecting device 8. Any of a variety of materials appropriate to orthodontic treatment (including rubbers, plastics, metals and composites) may be used in forming the closure member 26, depending upon its manner of association with the end 18 of the outer tube 10.

The closure member 26 defines a centrally disposed aperture 27 for slidingly receiving the piston rod 21. The diameter of the aperture 27 is preferably relatively closely matched to the diameter of the piston rod 21, to facilitate in proper guidance of the piston rod 21, yet is kept sufficiently loose so as not to interfere with movement of the piston 11. This, in turn, promotes free travel of the piston 11 during normal operating conditions. However, before the piston 11 can reach the end 18 of the outer tube 10, the piston body 20 will be brought into engagement with the leading edge 28 of the closure member 26, preventing further outward movement of the piston body 20 and preventing separation of the piston 11 from the outer tube 10.

The dimensions of the various components comprising the connecting devices 8, 9 will necessarily vary, depending upon variables such as the size of the patient's mouth and the treatment that is indicated. This will include variables such as the length (and diameter) of the outer tube 10, the force applied by the spring 24, and the shape and size of the clip portions 16, 22. Virtually any dimensions may be employed provided the selected dimensions are sufficient to provide appropriate forces for the treatment that is needed, appropriate structural integrity to the unit, and sufficient comfort for the patient.

As an example of typical dimensions, the outer tube 10 will have a length on the order of 25 mm, an outer diameter on the order of 3.5 mm, and an inner diameter on the order of 2.5 mm at the end 13 and 2.0 mm at the end 18 (defining the closure member 26). The end cap 12 will have an outer diameter on the order of 4.5 mm, an inner diameter on the order of 3.5 mm, and a length on the order of 5 mm. The piston 11 will include a piston head 20 having a length on the order of 2 mm and a diameter on the order of 2.5 mm, and a piston rod 21 having a length on the order of 17 mm and a diameter on the order of 2.0 mm. The spring 24 used in conjunction with this exemplary connecting device will have a length on the order of 20 mm. The corresponding closure member 26 of the outer tube 10 will have a length on the order of 2 mm and an inner diameter on the order of 2.0 mm. Each of the attachment clips 16, 22 is preferably disposed at an angle of 45° relative to an axis defined along the length of the connecting device (i.e., the outer body 10). The aperture 17 of the end cap 12 will typically have a diameter on the order of 0.050 inches and the aperture 23 of the piston 11 will typically have a diameter on the order of 0.030 inches. It is to be understood that the foregoing dimensions are provided only by way of example, and that these parameters may be freely varied to suit any of a variety of potential uses for the connecting devices 8, 9, as desired.

Referring again to FIGS. 1 and 2, attachment of the connecting devices 8, 9 to and between the upper and lower appliances 6, 7 (completing the orthodontic appliance 5) will now be described for the illustrative procedure that is shown. In substantially conventional fashion, the upper appliance 6 is attached to the upper teeth 3 by attaching (e.g., gluing or bonding) a plurality of supports 30 to the upper teeth 3, and by appropriately interconnecting the supports 30 with a common (arch) wire 31. The lower appliance 7 is similarly attached to the lower teeth 4 by fixing a plurality of supports 30 to the lower teeth 4, and by interconnecting the supports 30 with a common (arch) wire 32. To this point, the procedures involved are substantially conventional, and could employ any of a variety of known techniques to accomplish the end result which is desired.

The connecting devices 8, 9 are then fitted to and between the appliances 6, 7. The manner in which this is accomplished will depend upon the treatment that is intended. In the illustrative embodiment of FIGS. 1 and 2, the orthodontic appliance 5 is being used in its most common fashion, to treat protrusion of the upper teeth 3 relative to the lower teeth 4. In such case, the connecting devices 8, 9 are attached to and between the upper molar areas and the lower canine areas of the patient's teeth. However, it will be understood that similar techniques can be employed to accomplish other treatments, resulting in other placements for the connecting devices 8, 9 which are appropriate to such treatments.

The connecting devices 8, 9 are attached to the appliances 6, 7 with paired connectors 33, 34 for appropriately receiving the respective ends (the clip portions 16, 22) of the connecting devices 8, 9. Each connector 33 includes a tube 35a for slidingly receiving an end of the arch wire 31 and a tube 35b connected to the tube 35a, for receiving an anchor pin 36. The terminating end of each anchor pin 36 includes a ball stop 36a, which is preferably integral with the anchor pin 36. Each connector 34 employs the arch wire 32 of the lower appliance 7, in combination with a sliding ball 37 which bears against a crimpable stop 38 for engaging the arch wire 32. Of course, any of a variety of known connectors may be employed, apart from the connectors 33, 34, if desired.

Upon assembly, the anchor pins 36 are in turn passed through the apertures 17 of the end caps 12, and the corresponding tubes 35b of each connector 33. The anchor pins 36 are then bent over, crimping the clip portions 16 between the ball stops 36a of the anchor pins 36 and the tubes 35b of the connectors 33. The apertures 23 of the pistons 11 of the associated connecting devices are caused to slidingly engage the arch wire 32 which interconnects the supports 30 associated with the lower teeth 4. The crimpable stops 38 of the connectors 34 serve to appropriately limit movement of the engaged clip portions 22 of the connecting devices 8, 9 along the arch wire 32 which they engage, achieving the amount of activation that is required for a particular, orthodontic treatment. The connectors 33, 34 also advantageously permit the connecting devices 8, 9 to pivot about the connectors 33, 34, and the arch wires 31, 32, to a limited degree which assists in providing additional freedom of movement (and accordingly, comfort) to the patient. The amount of activation achieved by such structure can be varied, if desired, by adding stops (i.e., plural crimpable stops) to the arch wire 32. Resulting from such attachment, the connecting devices 8, 9 are allowed to slide along the arch wire 32 for a limited distance defined by the nearest adjacent supports 30.

The foregoing, coupled with an appropriately dimensioned connecting device (including the outer tube 10 and spring 24, the piston 11 and the clip portions 16, 22), is used to establish the structural relationships needed to ensure desired interaction between the various components comprising the orthodontic appliance 5, to achieve the orthodontic treatment which is desired. This includes providing appropriate compressive forces during "active" portions of the intended treatment (i.e., expansive, axially outwardly directed forces), as well as sufficient freedom of movement during "inactive" portions of the intended treatment.

To this end, and in accordance with the present invention, the degree of longitudinal movement permitted by the connectors 34 along the arch wire 32, and the length of the outer tube 10 of the connecting devices 8, 9 (coupled with a correspondingly sized spring 24), is preferably selected so that compressive forces are applied between the connectors 33, 34 of the arch wires 31, 32 when the mouth of the patient has been closed approximately halfway. In this way, appropriate forces are developed for achieving the treatment that is desired, and the forces that are produced are applied along a substantially horizontal vector, which is preferred for proper treatment. Unwanted movements resulting from the application of excessive forces away from the horizontal vector are avoided as a result, although limited (relatively small) forces in a vertical direction may be employed if appropriate for a particular orthodontic treatment (e.g., to achieve a slight intrusion of the upper molars).

What is more, this is achieved without promoting damage to the orthodontic appliance 5. Upon closure, the various elements of the connecting devices 8, 9 are configured to apply desired forces (resulting from action of the spring 24) to and between the connectors 33, 34 associated with the arch wires 31, 32, and to absorb (again resulting from action of the spring 24) forces which might tend to promote damage to the connecting devices 8, 9, to the connectors 33, 34, or to the arch wires 31, 32. As the patient's mouth is opened, telescoping movement of the outer tube 10 and the piston 11 is limited by the stop mechanism 25, preventing a separation of these two structures. Ordinarily, this would tend to limit the patient's ability to open the mouth, which is undesirable in terms of comfort, and which is potentially damaging to the connecting devices 8, 9, the connectors 33, 34, and the arch wires 31, 32. However, in accordance with the present invention, the sliding movement permitted by the clip portions 22 of the connecting devices 8, 9 and the connectors 34, along the arch wire 32, operates to prevent separation of the piston 11 from the outer tube 10 while also preventing hard contact between the piston 11 and the outer tube 10. In this way, stressful contact between the clip portions 16, 22 and the connectors 33, 34 is avoided irrespective of the position of the patient's mouth, between its fully opened and fully closed positions. This benefit is achieved while preventing separation of the telescoping outer tube 10 and piston 11, responsive to the blocking connection of the stop mechanism 25.

While the above-described configuration for the connecting devices 8, 9 is presently preferred, suitable connecting devices for implementing the improvements of the present invention may assume any of a variety of configurations. One such alternative embodiment connecting device 40, shown in FIG. 5A of the drawings, generally includes an outer body 41 for slidingly engaging a piston 42. The outer body 41 includes an integral clip portion 43, and has a uniform inner diameter for slidingly receiving the piston rod 44 of the piston 42. An end cap 45 is provided for engaging the end 46 of the piston rod 44. An outwardly disposed spring 24 is received between the outer body 41 and a clip portion 47 associated with the end 48 of the piston rod 44. Assembly of the connecting device 40 is accomplished by positioning the spring 24 over the piston rod 44 of the piston 42, and inserting the piston rod 44 through the outer body 41 so that the terminating end 46 extends from the outer body 41 as shown. The end cap 45 is then positioned over and fixed to the end 46 of the piston rod 44, completing the desired structure. The clip portions 43, 47 are then used to attach the connecting device 40 to and between the upper appliance 6 and the lower appliance 7 of the orthodontic appliance 5 to achieve desired orthodontic treatments (in substantially similar fashion to the connecting devices 8, 9).

Figure 5A:
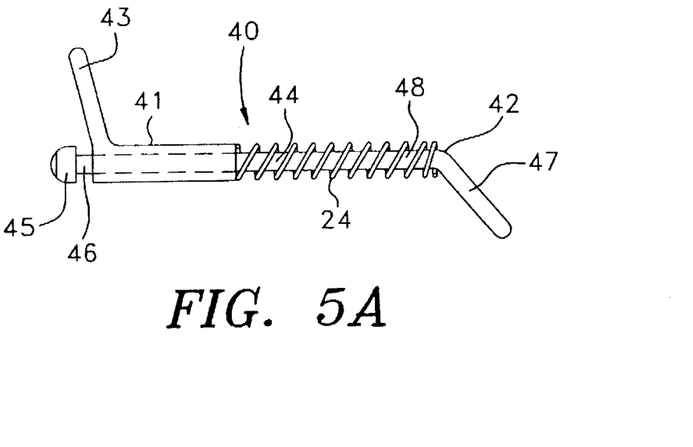
FIGS. 5A, 5B, 6, 7 and 8 are side elevational views showing alternative embodiment connecting devices of the present invention, with portions broken away to reveal internal construction.
Figure 5B:
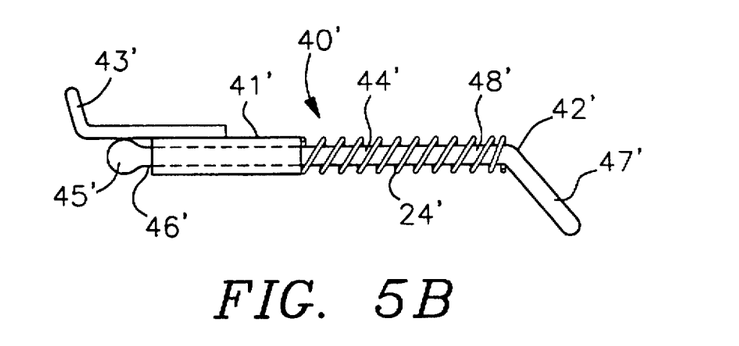

FIG. 5B shows an alternative for implementing the connecting device 40 of FIG. 5A. The connecting device 40' again generally includes an outer body 41' for slidingly engaging a piston 42'. However, in this case, the outer body 41' includes a separate clip portion 43', which is preferably welded to the exterior of the outer body 41', and an end portion 45' which is integral with the end 46' of the piston rod 44'. An outwardly disposed spring 24 is again received between the outer body 41' and a clip portion 47' associated with the end 48' of the piston rod 44'. To be noted is that a separate clip portion welded to its associated outer body may be used with other embodiments of the connecting device of this invention, if desired.

Assembly of the connecting device 40' is accomplished by inserting the piston rod 44', which is initially straight, through the outer body 41' so that the piston 44' extends from the outer body 41' as shown. The end portion 45' is then positioned for engagement with the outer body 41', serving to prevent separation of the two structures. The spring 24 is then positioned over the piston rod 44' of the piston 42', followed by formation of the clip portion 47', completing the desired structure. The clip portions 43', 47' are then used to attach the connecting device 40' to and between the upper appliance 6 and the lower appliance 7 of the orthodontic appliance 5 to achieve desired orthodontic treatments.

Figure 6:
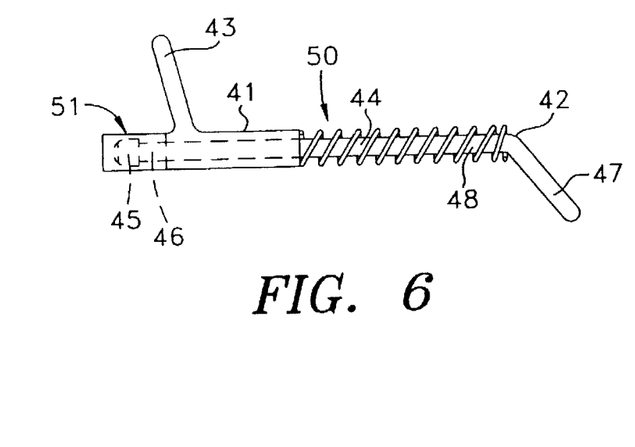

FIG. 6 shows a variation of the connecting device 40 of FIGS. 5A and 5B. In certain circumstances, and despite the smooth outer surface associated with the end cap 45, the potential exists for protruding structures of the connecting device 40 to cause irritation when worn by a patient. This can be corrected with the connecting device 50 shown in FIG. 6. The connecting device 50 is substantially similar to the connecting device 40, with the exception that the outer body 41 of the connecting device 50 includes an extension 51 for overlying the end cap 45 of the piston rod 44. By maintaining the end cap 45 (and the end 46 of the piston rod 44) within the enclosure of the extension 51, the potential for irritating surrounding portions of the patient's mouth is effectively precluded.

Figure 7:
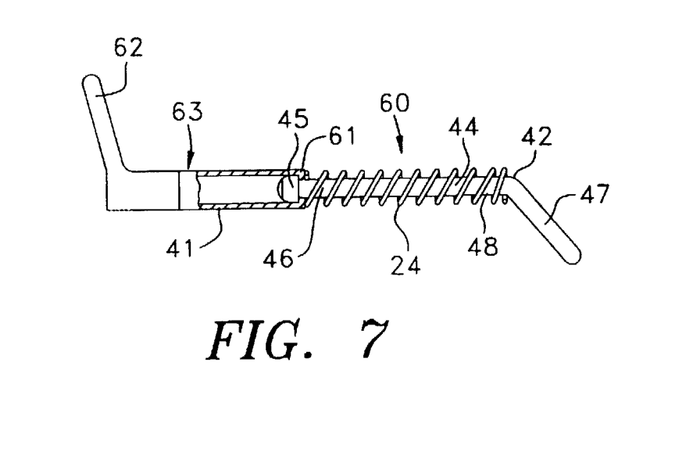

FIG. 7 shows yet another variation of the connecting devices 40, 40', 50 of FIGS. 5A, 5B and 6. The connecting device 60 again generally includes an outer body 41 for slidingly receiving a piston 42. However, in this embodiment, the end cap 45 is received against a flanged end 61 formed in the outer body 41 so that the end cap 45 (and the end 46 of the piston rod 44) remains enclosed within the outer body 41. An end cap 62 similar to the end cap 12 associated with the connecting devices 8, 9 is fitted to the end 63 of the outer body 41 to complete the connecting device 60.

Figure 8:
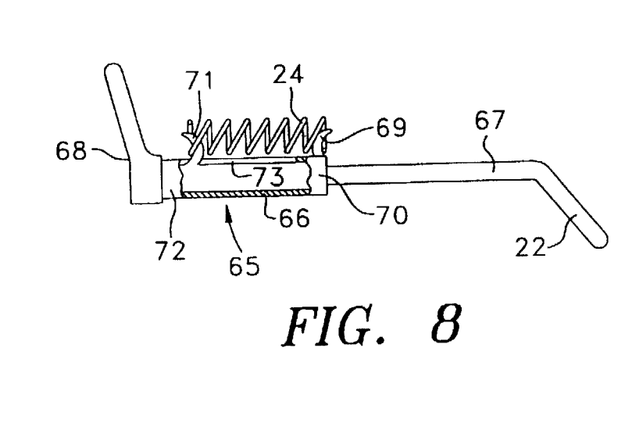

FIG. 8 shows yet another embodiment of a connecting device incorporating an externally disposed spring 24. The connecting device 65 again generally includes an outer body 66 for slidingly receiving a piston 67 within its confines. The outer body 66 again terminates in an end cap 68 including a clip portion 16, and the piston 67 terminates in a clip portion 22, for connection to and between the upper appliance 6 and the lower appliance 7 of the orthodontic appliance 5 to achieve desired treatments. A hook 69 extends from the end 70 of the outer body 66 opposing the end cap 68. Similarly, a hook 71 extends from the end 72 of the piston 67 opposing the clip portion 22, and slides within a slot 73 formed in the outer body 66. The spring 24 is connected to and between the hooks 69, 71, for achieving desired activation of the connecting device 70.

It will therefore be understood that various changes in the details, materials and arrangement of parts which have been herein described and illustrated in order to explain the nature of this invention may be made by those skilled in the art within the principle and scope of the invention as expressed in the following claims.

What is claimed is:

1. An element for connecting a first appliance of an orthodontic device and a second appliance of the orthodontic device, wherein the first appliance and the second appliance are capable of association with teeth of a patient for applying forces to and between the first appliance and the second appliance, and the teeth associated with the first appliance and the second appliance, wherein the connecting element comprises:

a body portion including an outer shell for defining a centrally disposed, hollow cavity, wherein a first end of the body portion includes means for connection with the first appliance;

a piston slidingly received in the hollow cavity of the body portion, and extending from a second end of the body portion opposite to the first end, wherein the piston includes a termination having means for connection with the second appliance; and a spring associated with the piston, for producing compressive forces between the connection means of the body portion and the connection means of the piston, for application to and between the first appliance and the second appliance of the orthodontic device, wherein the spring is externally associated with the body portion.

2. The connecting element of claim 1 wherein the piston includes a piston rod for slidingly engaging the hollow cavity of the body portion, and an end portion associated with a first end of the piston rod for retaining the piston rod within the hollow cavity of the body portion, wherein the piston rod includes a second end opposite to the first end which includes the termination for the piston.

3. The connecting element of claim 2 wherein the spring surrounds the piston rod, and is positioned between the body portion and the termination of the piston.

4. The connecting element of claim 2 wherein the body portion further includes an extension for enclosing the end portion, and the first end of the piston rod.

5. The connecting element of claim 2 wherein the body portion further includes a hook extending from an end adjacent to the second end of the piston rod, wherein the piston includes a hook extending from the first end of the piston rod, and wherein the spring is positioned between the hook of the body portion and the hook of the piston.

6. The connecting element of claim 2 wherein the end portion is an end cap engaging the first end of the piston rod.

7. The connecting element of claim 2 wherein the end portion is integral with the first end of the piston rod.

* * * * *